United States Patent
Price et al.

(10) Patent No.: US 10,925,828 B2
(45) Date of Patent: Feb. 23, 2021

(54) TOOTHPASTE COMPOSITION AND METHOD OF MAKING SAME

(71) Applicant: EWC & Associates, LLC, Phoenix, AZ (US)

(72) Inventors: Ginger Price, Phoenix, AZ (US); Martin Giniger, New York, NY (US)

(73) Assignee: EWC & Associates, LLC, Phoenix, AZ (US)

( * ) Notice: Subject to any disclaimer, the term of this patent is extended or adjusted under 35 U.S.C. 154(b) by 8 days.

(21) Appl. No.: 16/284,652

(22) Filed: Feb. 25, 2019

(65) Prior Publication Data

US 2019/0269606 A1    Sep. 5, 2019

Related U.S. Application Data

(60) Provisional application No. 62/637,208, filed on Mar. 1, 2018.

(51) Int. Cl.
| | |
|---|---|
| *A61K 8/92* | (2006.01) |
| *A61Q 11/00* | (2006.01) |
| *A61K 8/25* | (2006.01) |
| *A61K 8/34* | (2006.01) |
| *A61K 8/60* | (2006.01) |
| *A61K 8/29* | (2006.01) |
| *A61K 8/46* | (2006.01) |
| *A61K 8/73* | (2006.01) |

(52) U.S. Cl.
CPC ............... *A61K 8/922* (2013.01); *A61K 8/25* (2013.01); *A61K 8/29* (2013.01); *A61K 8/345* (2013.01); *A61K 8/463* (2013.01); *A61K 8/60* (2013.01); *A61K 8/73* (2013.01); *A61Q 11/00* (2013.01); *A61K 2800/43* (2013.01); *A61K 2800/805* (2013.01)

(58) Field of Classification Search
None
See application file for complete search history.

(56) References Cited

U.S. PATENT DOCUMENTS 4,701,319 A * 10/1987 Woo .................. A61K 8/73
424/49
10,149,815 B2 * 12/2018 Price ................ A61K 8/922

FOREIGN PATENT DOCUMENTS

JP    2000128751 A  *  5/2000

OTHER PUBLICATIONS

Gilbert et al (https://blog.charkit.com/understanding-rbd-coconut-oil-and-its-applications, Oct. 20, 2017). (Year: 2017).*

* cited by examiner

*Primary Examiner* — Celeste A Roney
(74) *Attorney, Agent, or Firm* — David Rosenbaum; Rosenbaum, IP, P.C.

(57) ABSTRACT

A toothpaste composition having a plant oil constituent together with white or a close shade of white coconut shell activated charcoal constituent is disclosed herein.

15 Claims, 1 Drawing Sheet

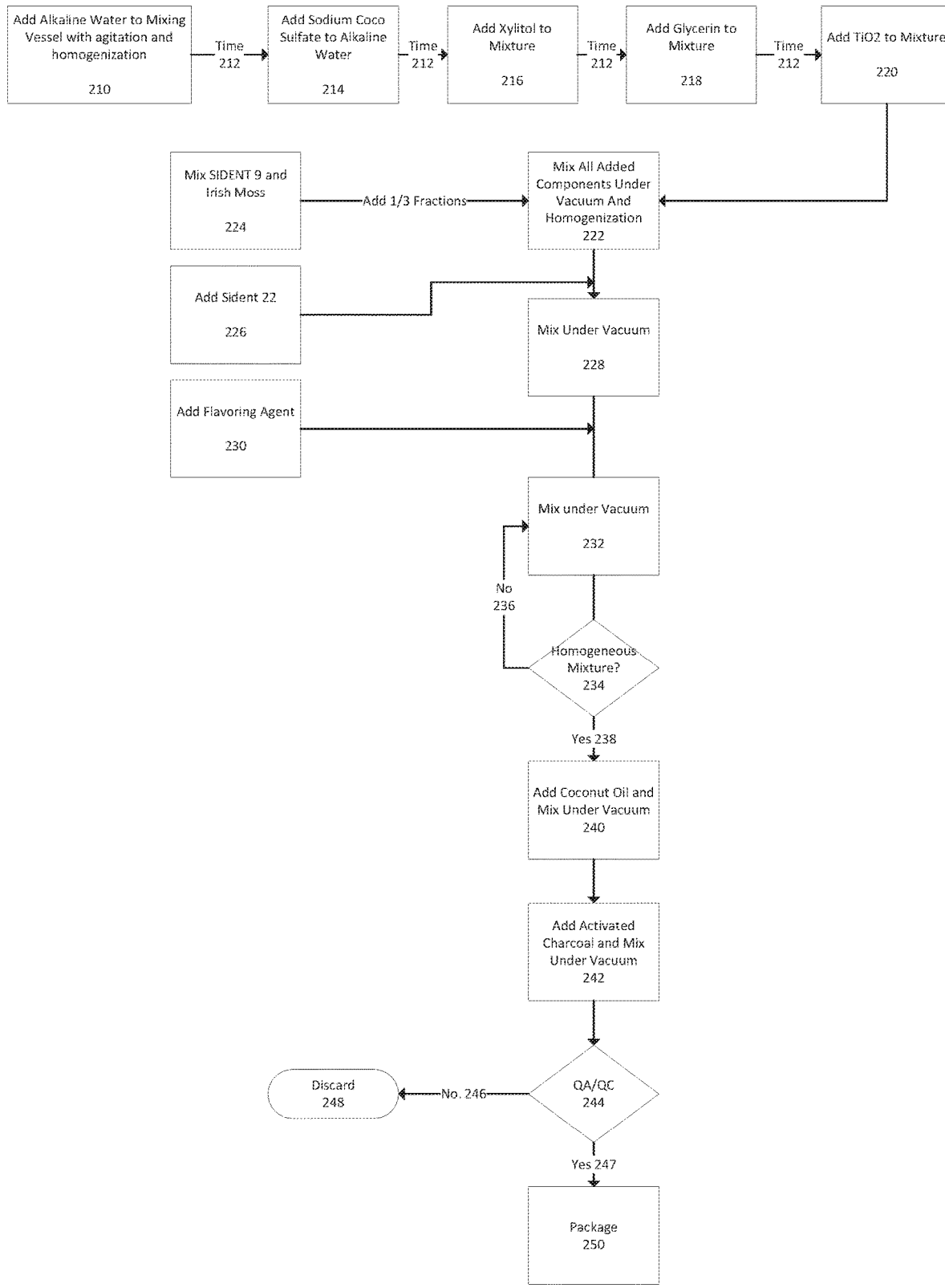

TOOTHPASTE COMPOSITION AND METHOD OF MAKING SAME

CROSS-REFERENCE TO RELATED INVENTIONS

The present invention claims priority to U.S. Provisional Application Ser. No. 62/637,208, file Mar. 1, 2018 and is related to commonly assigned U.S. patent application Ser. No. 15/207,406 filed Jul. 11, 2016, published as US2017/0007533 on Jan. 12, 2017, all of which is hereby incorporated by reference in their entireties.

BACKGROUND

The present invention pertains generally to compositions for tooth and oral care and pertains particularly to toothpaste compositions and methods of making toothpaste compositions.

Oral health care and tooth cleaning dates back before 2000 B.C. in the Middle East, when abrasives such as crushed bone, crushed egg, and oyster shells were used to clean debris from teeth. Prior to the 1850s, toothpastes were actually powders. During the 1850s, a toothpaste-in-a-jar called Crème Dentifrice was developed. Betel nut was included in toothpaste in England in the 1800s, and in the 1860s a home encyclopedia described homemade toothpaste that used ground charcoal.

Tooth powder, available from the late 18th century until the latter part of the 19th century, comprised charcoal and powdered bark and was packaged in a ceramic container as a powder or paste. Brushes, twigs, fabric, or the user's finger could apply such powder. A dentist then added soap to toothpaste in 1824. Chalk was subsequently added to the mixture. In 1873, the Colgate Company started mass-producing toothpaste with more pleasing flavor in jars. Colgate introduced toothpaste in a tube similar to modern-day toothpaste tubes in the 1890s. Such pre-mixed toothpastes were first marketed in the 19th century, but did not surpass the popularity of tooth powder until World War I.

Until 1945, toothpastes contained soap. After that time, other ingredients such as sodium lauryl sulfate made the paste into a smooth emulsion and replaced soap. By 1900, a paste made of hydrogen peroxide and baking soda was recommended. In the second half of the twentieth century modern toothpastes were developed to help prevent or treat specific diseases and conditions such as tooth sensitivity. Toothpastes with very low abrasiveness were also developed and helped prevent problems caused by overzealous brushing.

The breakthrough that transformed toothpaste into the crucial weapon against tooth decay was the finding that fluoride could dramatically reduce cavities. Fluoride was added to toothpaste in the early 1960s, and soluble calcium fluoride was added some 20 years later.

Americans, it is estimated, brush their teeth nearly 200 billion times a year and spend more than $1.6 billion on products relating to such activity. Toothpastes today typically contain fluoride, coloring, flavoring, and sweetener, as well as ingredients that render the toothpaste a smooth paste. When used, the paste foams, stays moist and provides substantially full dental coverage within the user's mouth.

Modern toothpaste, which contains abrasives that physically scrub away plaque, works with a toothbrush to clean teeth and impedes the growth of plaque bacteria. Most of the cleaning is achieved by the mechanical action of the toothbrush, not by the toothpaste. The chemicals that hinder the growth of plaque bacteria include ingredients such as natural xylitol and artificial triclosan. In addition to removing food stains from teeth, toothpaste abrasives polish tooth surfaces.

Mouth and dental disease is often caused by bacteria resident in the mouth. These bacteria, if left unchecked, cause inflammation of the gums, mucosal lining, palate, tongue and tooth decay. Regular dental and oral care helps to maintain healthy levels of bacterial prevent oral inflammation and reduces the likelihood of oral and dental disease and the attendant medical treatment and pain associated with it.

Coconut oil has been used in oral health practices for thousands of years to aid in removal of bacteria from the mouth. For many years, oil pulling, including using coconut oil, has been employed in Ayurvedic medicine as a method of oral detoxification. Oil pulling entails swishing a quantity of oil in the mouth for 10-20 minutes and pushing and sucking the oil through the teeth. Oil pulling has been used adjunctive to brushing and flossing as part of an oral care regimen. The use of coconut oil has been proven effective in this line of use, and therefore, has been incorporated into oral health practices. Moreover, using coconut oil in dental care helps people maintain good oral and dental health without using fluoride. Understandably, a daily regimen that requires swishing, pushing and sucking oil through the teeth is widely regarded as being an undesirable daily practice.

Activated charcoal has been used for a number of years as a dentifrice and whitening agent for the teeth. Recently, coconut shell activated charcoal has seen a resurgence in use as dental powders and in toothpaste compositions. Charcoal, including coconut shell activated charcoal is black in appearance, rendering the dentifrice compositions black in color; a color which is typically unappealing to most people in a personal care product, particularly oral care products. Heretofore, it has been unknown to the applicants hereof, to employ coconut shell activated charcoal that is white or a close shade of white in a toothpaste composition, such that the toothpaste is not black in color.

Thus, it is recognized that it is desirable to provide a toothpaste composition having a coconut oil constituent together with white or a close shade of white coconut shell activated charcoal constituent.

SUMMARY OF THE INVENTION

It is an objective of the present invention to provide a fluoride-free toothpaste composition having a coconut oil base and including a fraction of white activated coconut husk charcoal.

It is a further objective of the present invention to provide a toothpaste composition without an aloe component.

It is a further objective of the present invention to provide a method of making the inventive fluoride-free toothpaste having a coconut oil base and including a fraction of white activated coconut husk charcoal.

The structure, overall operation and technical characteristics of the present invention will become apparent with the detailed description of preferred embodiments and the illustration of the related drawings as follows.

The methods, systems, and compositions are set forth in part in the description which follows, and in part will be obvious from the description, or can be learned by practice of the methods, apparatuses, and systems. The advantages of the methods, systems, and compositions will be realized and attained by means of the elements and combinations particularly pointed out in the appended claims. It is to be understood that both the foregoing general description and the following detailed description are exemplary and explanatory only and are not restrictive of the methods, compositions, and systems, as claimed.

BRIEF DESCRIPTION OF THE DRAWINGS

In the accompanying FIGURE, like elements are identified by like reference numerals among one of embodiments of the present invention.

FIG. 1 is a flowchart illustrating the method of making the inventive toothpaste composition.

DESCRIPTION OF THE EMBODIMENTS

The following description of the toothpaste composition and method of making the inventive toothpaste composition is exemplary, is intended to allow one of ordinary skill in the art to practice the invention without undue experimentation and is intended to be non-limiting. All percentages are expressed in weight percent (wt %) unless otherwise stated.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

The words "about," "substantially," or "generally" when used to describe numerical values are intended to include ±5% the stated numeral value, values or value ranges.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, and biochemical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The composition of the present invention is an admixture of alkaline water, sulfated fatty acids from coconut oil, at least one sweetening agent, at least one humectant, at least one whitening pigment, at least one silica, at least one flavoring agent, a thickening agent, a natural plant oil having a ratio of hypocholesterolemic fatty acids to hypercholesterolemic fatty acids in the range of about 10-22 wt % hypocholesterolemic fatty acids to about 70-75 wt % hypercholesterolemic fatty acids, and activated charcoal. The constituent components of the inventive toothpaste composition are sequentially admixed together under vacuum, with periods of homogenization and periods without homogenization, until a paste-like consistency is achieved, validated and packaged.

The silica component of the invention is preferably a hydrated silicon dioxide. Silicon dioxides particularly useful in the present invention include the following: ZEOTHIX 265, ZEOTHIX 95, or ZEOTHIX 177; ZEODENT 103, ZEODENT 113, ZEODENT 114, ZEODENT 115, ZEODENT 118, ZEODENT 119, ZEODENT 165, or ZEODENT 9175, (Evonik Industries AG, Essen, Germany). Silicas suitable for use in the present invention, as well as processes suitable for preparing them, are set forth in U.S. Pat. Nos. 3,893,340, 4,340,583, 5,225,177, and 6,616,916, as well as U.S. patent Publication No. 2003/0131536 A1. Additionally, silicon dioxides useful or potentially useful in the present invention are available from Ineos Silicas, Warrington, England, marketed under the trademark SORBOSIL; from Rhodia Silica Systems, Lyon, France, marketed under the trademarks TIXOSIL and ORALSIL V and from Grace, Columbia, Md. under the trademark SIDENT.

Alternatively, or additionally, the silicon dioxide component may also be an amorphous silica or fumed, also known as pyrogenic, silica (CAS number 112945-52-5).

Table 1, below, shows the details of a preferred formulation of the coconut oil toothpaste. The toothpaste contains about 35.5% alkaline water, about 27.75% coconut oil, about 15.4% hydrated silica SIDENT 9 (Grace, Columbia, Md.), about 2.8% hydrated silica SIDENT 22s (Grace, Columbia, Md.), about 10.5% glycerin, about 4% xylitol, about 1.4% Irish moss, about 0.7% sodium coco sulfate, about 0.65% titanium dioxide, about 0.7% activated coconut white charcoal, and about 0.6% flavoring.

Table 1 also sets forth alternative ranges of the individual constituents in the inventive toothpaste composition which are useful in the present invention.

TABLE 1

| Constituent | Amount (wt %) | Acceptable Range (wt %) |
|---|---|---|
| Water | 35.5% | 20-40% |
| Coconut Oil | 27.75% | 20-40% |
| Silica SIDENT 9 | 15.4% | 10-20% |
| Silica SIDENT 22s | 2.8% | 1-4% |
| Glycerin | 10.5% | 10-20% |
| Xylitol | 4% | 3-5% |
| Irish Moss | 1.4% | 1-3% |
| Activate Coconut White Charcoal | 0.7% | 0.05-2% |
| Sodium Coco Sulfate | 0.7% | 0.05-2% |
| Titanium Dioxide | 0.65% | 0.05-2% |
| Flavoring | 0.6% | 0.01-2% |

SIDENT 9 is a silicon dioxide having an average particle size of about 9 microns (measured by ISO 13320-1), a density of about 0.430 g/cc (measured by ISO 787-11), a specific surface area of 45 m$^2$/g (measured by ISO 9277) and a pH of 6.9 (measured by ISO 787-9, 5% in water). SIDENT 9 is an abrasive with moderate hardness and moderate thickening properties.

SIDENT 22s a silicon dioxide having an average particle size of about 13.5 microns (measured by ISO 13320-1), a density of about 0.0900 g/cc (measured by ISO 787-11), a specific surface area of 190 m$^2$/g (measured by ISO 9277) and a pH of 6.59 (measured by ISO 787-9, 5% in water). SIDENT 22s influences the rheological properties of the inventive toothpaste composition and improves the cleaning efficiency of the SIDENT 9 in the inventive toothpaste composition.

The water is preferably alkaline water having a pH between about 8.0 and 9.0, however, alkaline water in the range of pH between about 7.5 to about 10 may also be used.

The plant oil constituent is preferably both organic and food grade. The most preferred plant oil is coconut oil having between about 11 to about 22 wt % of hypocholesterolemic fatty acid residues, between about 9 to about 18 wt % neutral fatty acid residues, for example C8, C10 or C18 fatty acids, about 46 to about 48 wt % of moderately hypercholesterolemic fatty acids residues, for example C12 fatty acids, and about 24 to about 27 wt % of fatty acid residues having strong hypercholesterolemic effect, for example C14 and C16 fatty acids.

Alternative oils useful with the present invention include palm kernel oil, babassu oil and fractions thereof. It has been found that oils that are solid at room temperature are preferred.

In accordance with one aspect of the present invention, glycerin is employed as a sweetening agent and a humectant in the toothpaste composition of the present invention. Alternative suitable humectants useful with the present invention include edible polyhydric alcohols, such as, for example, sorbitol, xylitol, propylene glycol, other edible polyols and mixtures of the foregoing. Where sorbitol is employed it may be employed as a 70% aqueous solution. A mixture of sorbitol, a mixture of glycerin, and a mixture of sorbitol and glycerin are particularly useful as the humectant component of the inventive toothpaste composition.

While xylitol is a preferred sweetener, alternative sweetening agents may be used in the composition of the present invention. Suitable alternative sweetening agents include sucrose, lactose, maltose, sorbitol, sodium cyclamate, perillartine, L-aspartyl-L-phenylalanine methyl ester, levulose, dextrose, D-tryptophan, dihydrochalcones, acesulfame and saccharine.

Irish moss is employed as a thickening agent in one aspect of the present invention. Irish moss, (*Chondrus crispus*), also called carrageen, is a species of red algae (family Gigartinaceae) that grows abundantly along the rocky parts of the Atlantic coast of the British Isles, continental Europe, and North America. The principal constituent of Irish moss is carrageenan, a gelatinous substance which can be extracted by boiling. Carrageenan is often used as an emulsifying and suspending agent in pharmaceuticals, food products, cosmetics, and shoe polishes. In the present invention, Irish moss is employed in its desiccated powder form when admixed into the composition of the present invention.

Titanium dioxide is used as a whitening pigment agent in the composition of the present invention. The titanium dioxide may be ilmenite, rutile or anatase or combinations of the same. Preferably, the titanium dioxide component may have an average particle size less than about 250 nm, and most preferably have an average particle size less than about 100 nm.

A wide variety of flavoring agents may be used in the toothpaste composition of the present invention. Examples of suitable flavoring agents include, without limitation, coconut flavoring extract, oil of wintergreen, oil of peppermint, oil of spearmint, oil of *sassafras* and oil of clove.

Turning now to the method of making the inventive toothpaste composition 200, which is described with reference to the process flow chart at FIG. 1. All process steps are conducted at standard room temperature pressure, unless otherwise specified. The alkaline water is first added to a clean and sanitized vessel 210. Successively, at time intervals 212, which are preferably at least about 3-10 minutes, most preferably about 5, between successive additions, the plant fatty acids, e.g., sodium coco sulfate 214, the sweetening agent, e.g., xylitol 216, the humectant, e.g., glycerin 218 and whitening pigment, e.g., titanium dioxide 220 are successively added to the vessel with sweep agitation and homogenization. The sweep agitation frequency is preferably about 16±2 RPM. Once all ingredients have been added, mixing continues under vacuum at the preferred sweep agitation frequency for about an additional 30 minutes to prepare a first mixture 222.

The Irish moss and a first silica component, e.g., SIDENT 9, are blended in a separate vessel 224. It is preferable to mix one-third portions of each component successively until the entire quantity of both components are fully mixed as a second mixture. The Irish moss and first silica component second mixture is then added to the first mixture. It is preferably to add one-third fractions of the second mixture successively to the first mixture under vacuum, sweep agitation and homogenization, creating a third mixture. This third mixture is then allowed to mix for about 7-15 minutes, preferably about 10 additional minutes.

The second silica component, e.g., SIDENT 22s, is then added to the third mixture in the main vessel and mixing continues under vacuum and homogenization for about an additional 7-15, preferably about 10, additional minutes, thereby forming a fourth mixture.

Once the fourth mixture in the main vessel is uniformly mixed, at least one flavoring agent is added 230 and mixing continues under vacuum until the mixture has a homogenous consistency 234. If a homogenous consistency is not achieved 236, the fourth mixture is mixed for an additional period of time. Once the homogenous consistency is achieved 238, the plant oil, e.g., coconut oil is added and mixed under vacuum 240 without homogenization for a period of time until fully blended.

After the plant oil, e.g., coconut oil is mixed, the activated charcoal component, preferably activated coconut charcoal, most preferably, activated coconut charcoal that has been bleached and is white or nearly white in appearance, is added 242 and mixed, under vacuum and without homogenization, at a speed less than the preferred sweep speed, i.e., 16±2 RPM, sufficient to disperse the activated charcoal particles generally uniformly throughout the admixture.

Once the activated charcoal has been dispersed in the admixture, the composition is in a paste-like consistency, the composition then undergoes quality assurance and quality control (QA/QC) testing 244 to validate its suitability for oral use and market release. If the QA/QC testing does not pass 246, the batch is discarded 248. If the QA/QC testing passes 247, the composition is either bulk packaged or filled into squeeze or pump tubes for labeling and sale.

Additionally, a preferred embodiment of the toothpaste with at least 40% of natural coconut oil has been shown to have a strong antimicrobial effect, as well as satisfactory whitening and breath freshening effects. A clinical study of this preferred embodiment shows that the embodiment killed 99% of all microorganisms tested. In contrast, the placebo and the control toothpaste (the Crest™ anti-cavity toothpaste) did not show antimicrobial activity against any of the 23 tested microorganisms. Furthermore, this embodiment was the only formulation in the study that had activity against Grain-negative bacteria (*Pseudomonas aeruginosa*) which is a critical bacterial species that contributes to periodontal disease. Therefore, the preferred toothpaste can be used to effectively prevent oral inflammation caused by bacteria.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A toothpaste composition, comprising: alkaline water, plant oil, silica, a humectant, a sweetening agent, a thickening agent, sodium coco sulfate, a whitening agent, and activated bleached coconut shell charcoal at about 0.05-2.0 wt %; wherein the plant oil is a coconut oil and the coconut oil has between about 10-22 wt % hypocholesterolemic fatty acids, between about 9 to about 18 wt % neutral fatty acid residues, wherein the neutral fatty acids are C8, C10 or C18 fatty acids, between about 46 to about 48 wt % of moderately hypercholesterolemic fatty acids residues, wherein the moderately hypercholesterolemic fatty acids residues are C12 fatty acids, and between about 24 to about 27 wt % of fatty acid residues having strong hypercholesterolemic effect, wherein the strong hypercholesterolemic effect fatty acid residues are C14 and C16 fatty acids.

2. The toothpaste composition according to claim 1, wherein the silica is hydrated silicon dioxide.

3. The toothpaste composition according to claim 1, wherein the humectant is selected from the group consisting of edible polyhydric alcohols, edible polyols and mixtures thereof.

4. The toothpaste composition according to claim 3, wherein the humectant is selected from the group consisting of glycerin, sorbitol, xylitol, propylene glycol, and mixtures thereof.

5. The toothpaste composition according to claim 4, wherein the humectant further comprises a mixture of sorbitol and glycerin in a 70% aqueous solution.

6. The toothpaste composition according to claim 1, wherein the sweetening agent is selected from the group consisting of xylitol, sucrose, lactose, maltose, sorbitol, sodium cyclamate, perillartine, L-aspartyl-L-phenylalanine methyl ester, levulose, dextrose, D-tryptophan, dihydrochalcones, acesulfame and saccharine.

7. The toothpaste composition according to claim 1, wherein the thickening agent further comprises carrageenan.

8. The toothpaste composition according to claim 1, wherein the whitening agent further comprises titanium dioxide.

9. The toothpaste composition according to claim 5, wherein the activated bleached coconut shell charcoal is generally uniformly throughout the toothpaste composition.

10. The toothpaste composition according to claim 9, wherein the alkaline water is present at about 20 to about 40 wt % of the toothpaste composition.

11. The toothpaste composition according to claim 10, wherein the silica is present at about 10 to about 24 wt % of the toothpaste composition.

12. The toothpaste composition according to claim 11, further comprising a first silica present at about 10 to about 20 wt % of the composition and a second silica present at about 1 to about 4 wt % of the toothpaste composition.

13. The toothpaste composition according to claim 12, wherein the humectant is present at about 10 to about 20 wt % of the toothpaste composition.

14. The toothpaste composition according to claim 13, wherein the sodium coco sulfate is present at about 0.05 to about 2 wt % of the toothpaste composition.

15. A toothpaste composition comprising, alkaline water, coconut oil, silica, a humectant, a sweetening agent, a thickening agent, sodium coco sulfate, a whitening agent, and activated bleached coconut shell charcoal;

the alkaline water is present at about 20 to about 40 wt % of the toothpaste composition;

the coconut oil is present at about 20 to about 40% of the toothpaste composition;

wherein the humectant further comprises a mixture of sorbitol and glycerin in a 70% aqueous solution, and the humectant is present at about 10 to about 20 wt % of the toothpaste composition;

the sodium coco sulfate is present at about 0.05 to about 2 wt % of the toothpaste composition;

the whitening agent is present at about 0.05 to about 2 wt % of the toothpaste composition;

the silica comprises a first silica present at about 10 to about 20 wt % of the composition and a second silica present at about 1 to about 4 wt % of the toothpaste composition;

the humectant is present at about 10 to about 20 wt % of the toothpaste composition;

the sweetening agent is present at about 3 to about 5 wt % of the toothpaste composition;

the activated bleached coconut shell charcoal is present at about 0.05 to about 2 wt % of the toothpaste composition; and wherein the sodium coco sulfate is present at about 0.05 to about 2 wt % of the toothpaste composition.

* * * * *